United States Patent [19]
Daftary

[11] Patent Number: 5,213,502
[45] Date of Patent: May 25, 1993

[54] INTERLOCKABLE TWO-PIECE IMPRESSION COPING FOR ANATOMICAL DENTAL ABUTMENT RESTORATIVE SYSTEMS

[76] Inventor: Fereidoun Daftary, 50 N. La Cienega Blvd., No. 206, Beverly Hills, Calif. 90211

[21] Appl. No.: 896,613

[22] Filed: Jun. 10, 1992

[51] Int. Cl.$^5$ .................... A61C 13/12; A61C 13/225; A61C 8/00
[52] U.S. Cl. .................................... 433/172; 433/173; 433/214
[58] Field of Search ............... 433/172, 173, 174, 175, 433/176, 214

[56] References Cited
U.S. PATENT DOCUMENTS

| | | | |
|---|---|---|---|
| 3,732,621 | 5/1973 | Bostrom | 433/174 |
| 4,713,003 | 12/1987 | Symington et al. | 433/173 |
| 4,713,004 | 12/1987 | Linkow et al. | 433/174 |
| 4,955,811 | 9/1990 | Lazzara et al. | 433/173 |
| 5,015,186 | 5/1991 | Detsch | 433/173 |
| 5,100,323 | 3/1992 | Friedman | 433/173 |

FOREIGN PATENT DOCUMENTS 0438984 7/1991 European Pat. Off. .

*Primary Examiner*—Gene Mancene
*Assistant Examiner*—Nicholas D. Lucchesi
*Attorney, Agent, or Firm*—Thomas I. Rozsa; Dong Chen

[57] ABSTRACT

The present invention is an interlockable two-piece impression coping for anatomical dental abutment restorative systems. It includes a bolt member and a coping member having complementary intercoupling members respectively, which are disengaged when the coping member is fully fastened to the dental component by the bolt member. The present invention is also a method of attaching an impression coping to a dental component of an anatomical dental abutment restorative system for making an impression. The essential steps of the present invention method include first intercoupling the bolt member and the coping member, and then attaching the coping member to the dental component and fastening the coping member to the dental component by the bolt member, while having their complementary intercoupling members disengaged.

22 Claims, 3 Drawing Sheets

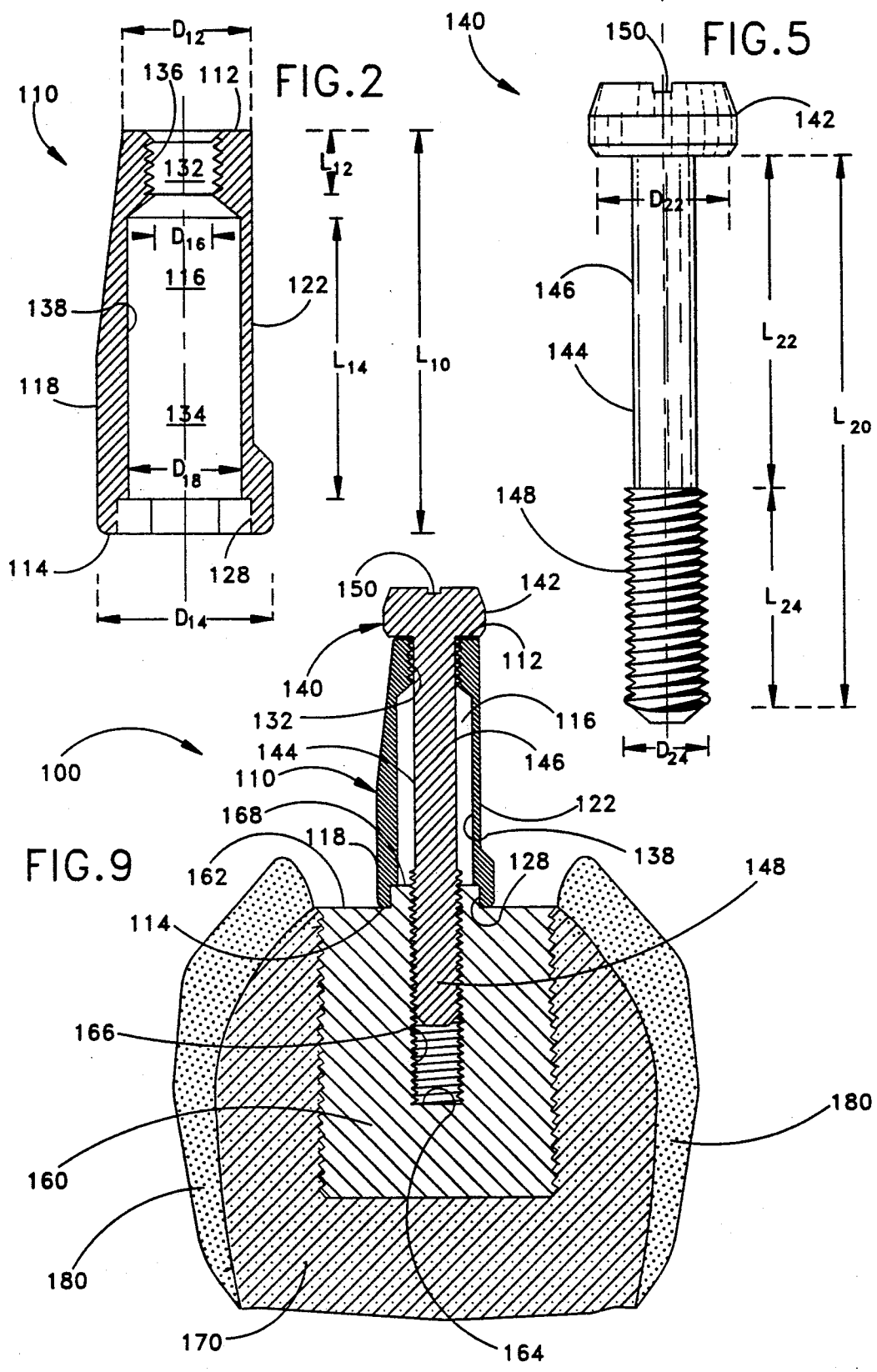

INTERLOCKABLE TWO-PIECE IMPRESSION COPING FOR ANATOMICAL DENTAL ABUTMENT RESTORATIVE SYSTEMS

BACKGROUND OF THE INVENTION

1. Field of The Invention

The present invention relates to the field of anatomical dental restorative systems. More particularly, the present invention relates to the field of impression copings for single-tooth prosthodontics restoration systems.

2. Description of The Prior Art

Anatomical dental restorative systems are commonly used today in single-tooth prosthodontics restorations. Generally, a single-tooth prosthodontics restoration involves the following procedures. First, a dental fixture is implanted into a patient's jawbone. The implant fixture typically has a hole with screw threads for receiving a screw bolt. The exposed end of the implant fixture typically further has a hexagonal interface for defining the orientation of the attachment of a tooth analogue. An impression coping is then attached to the implant fixture to make an impression for transferring to a working cast the natural dentition as well as both the exact position and the exact rotational alignment of the hexagonal interface of the implant fixture. Once the impression is made, it is removed from the patient's oral cavity in the patient's mouth and the impression coping is also removed. The impression coping is then attached to an analogue of the implant fixture and inserted back into the impression, and dental stone or die material is poured in to make the working cast for constructing the tooth analogue. The tooth analogue is finally attached to the implant fixture by a dental abutment.

To obtain the best fitting tooth analogue, it is critical to duplicate both the accurate position of the implant fixture and the rotational alignment of the hexagonal interface of the implant fixture. Therefore, it is very important to prevent both the relative rotation between the impression coping and the implant fixture and the relative rotation between the impression and the impression coping when the impression is made. In order to do so, the impression coping often has a complementary hexagonal interface for establishing non-rotatable engagement with the hexagonal interface of the implant fixture. In addition, the impression coping often has flat exterior surfaces for establishing non-rotatable engagement with the impression.

U.S. Pat. No. 4,955,811 issued to Lazzara et al. on Sep. 11, 1990 for "Non-Rotational Single Tooth-Prosthodontics Restoration" (hereafter the "Lazzara Patent") has disclosed a two-part impression coping, including a coping part and a bolt part. The coping part has a generally cone-shaped body with a narrow top end and a widened bottom end, where the widened bottom end has a male hexagonal interface for fitting snugly with the female hexagonal interface of the implant fixture. The exterior surface of the coping part has a flattened side to restrain the rotation of the impression.

The coping part of the Lazzara Patent further comprises a smooth bore extending through its body from the top end to the bottom end. The entirely smooth bore accommodates the bolt part. The bolt part has screw threads which match the screw threads in the hole of the implant fixture. Once the coping part is placed on the implant fixture and the hexagonal interfaces of the coping part and the implant fixture are properly engaged, the bolt part is extended through the smooth bore of the coping part and threaded into the implant fixture to secure the coping part onto the implant fixture for making the impression.

A problem experienced by dental practitioners which is associated with the Lazzara Patent two-piece type of design of the impression coping, is that the coping part and the bolt part are completely separated and unattachable. The separation and unattachableness of the coping part and the bolt part create several disadvantages. For example, it increases the possibility of mismatching the coping parts and the bolt parts of the impression copings which have different dimensions and specifications. In addition, since the bolt part is introduced into a patient's oral cavity after the coping part is seated on the implant fixture, it increases the difficulty of handling the bolt part and aligning it with the central bore of the coping part. Moreover, it increases the possibility of losing the bolt part in the patient's oral cavity.

Therefore, it is desirable to have an improved type of two-piece impression coping which utilizes a pair of separable but also interlockable coping and bolt pieces to overcome the above identified disadvantages.

SUMMARY OF THE INVENTION

The present invention is an interlockable two-piece impression coping for anatomical dental abutment restorative systems.

The primary novelty and uniqueness of the present invention two-piece impression coping is that its coping member and its bolt member are interlockable, and the interlocking feature is compatible with not only the hexagonal interface between the coping member and the dental implant fixture, but also the threaded engagement of the bolt member and the implant fixture.

It is known that two-piece type impression coping has been utilized in the process of anatomical dental restorations. More particularly, the two-piece type impression coping currently available includes a coping member and a bolt member. The coping member has a thoroughly smoothed bore for allowing the bolt member to extend through so that the bolt member can be threaded into the dental implant fixture to fasten the coping member to the implant fixture.

It has been discovered according to the present invention, however, that it will be beneficial to make the coping member and the bolt member of the impression coping not only separable, but also interlockable. Making the two pieces of the impression coping interlockable can prevent mismatching the pieces of different impression copings, ease the effort of aligning the two pieces in a patient's oral cavity, and reduce the chance of losing the bolt member in the patient's oral cavity.

It has also been discovered, according to the present invention, that if instead of having a smooth bore, the coping member of the two-piece impression coping has a central bore with screw threads, then when the bolt member of the two-piece impression coping is extended through the central bore of the coping member, the bolt member can be threadedly engaged with the coping member so that they are interlocked with each other.

However, it has further been discovered, according to the present invention, that if the bolt members are threadedly engaged with both the coping member and the dental implant fixture, then the threaded relationship between the coping member and the bolt member is incompatible with the hexagonal interface between the coping member and the implant fixture. This is because there are three interconnections or cross-engagements between the three pieces, i.e., the coping member, the bolt member and the implant fixture. The bolt member is threadedly engaged with both the coping member and the implant fixture, and the coping member is hexagonally engaged with the implant fixture. On the one hand, when the bolt member has a threaded relationship with the coping member, it applies not only a translational force but also a torque to the coping member. The translational force will act to fasten the coping to the implant fixture, but the torque will act to rotate the coping about the implant fixture. On the other hand, the coping member should not have any relative rotation about the implant fixture and that is the function of the hexagonal interface between them. Therefore, if when the bolt member is threadedly engaged with the implant fixture, it is still threadedly engaged with the coping member, then the latter engagement will act against the function of the hexagonal interface between the coping member and the implant fixture.

It has additionally been discovered, according to the present invention, that if the bolt member is divided into two sections including an upper smooth section and a lower threaded section, but the central bore of the coping member is divided into two sections including an upper threaded section and a lower smooth section which are opposite to two sections of the bolt member, then when the bolt member is initially extended into the central bore of the coping member from the upper end of the coping member, the lower threaded section of the bolt member will threadedly engage with the upper threaded section of the coping member. However, when the bolt member is further extended into the central bore of the coping member, the lower threaded section of the bolt member will disengage from the upper threaded section of the coping member and align with the lower smooth section of the coping member, and there will no longer be a threaded relationship between the bolt member and the coping member because their respective threaded portions are offset from each other. Therefore, since the bolt member is threadedly engaged with the implant fixture and it is no longer threadedly engaged with the coping member, there is no action or force against the function of the hexagonal interface between the coping member and the implant fixture.

It is therefore a primary object of the present invention to provide an interlockable two-piece impression coping for anatomical dental abutment restorative systems. The interlockable feature of the present invention impression coping will prevent the pieces of different impression copings from being mismatched, effect the alignment of the two pieces in a patient's oral cavity, and reduce the chance of dropping the bolt member into the patient's oral cavity.

It is also an object of the present invention to provide an interlockable two-piece impression coping for anatomical dental abutment restorative systems, where the central bore of the coping member has inner screw threads engagable with the outer screw threads of the bolt member, so that the coping member and the bolt member can be threadedly engaged and thereby interlocked.

It is a further object of the present invention to provide an interlockable two-piece impression coping for anatomical dental abutment restorative systems, where the coping member is only threadedly engaged with the bolt member when the bolt member has not yet threadedly engaged with the dental implant fixture. When the bolt member is threadedly engaged with the implant fixture, the coping member is no longer threadedly engaged with the bolt member to avoid any incompatibility with the hexagonal interface between the coping member and the implant fixture.

It is an additional object of the present invention to provide an interlockable two-piece impression coping for anatomical dental abutment restorative systems, where the bolt member is divided into an upper smooth section and a lower threaded section, but the central bore of the coping member is divided into an upper threaded section and a lower smooth section. When the bolt member is extended into the central bore of the coping member from the upper end of the coping member, the lower threaded section of the bolt member will initially be threadedly engaged with the upper threaded section of the coping member. When the bolt member is further extended into the central bore of the coping member, the lower threaded section of the bolt member will be offset from the upper threaded section of the coping member and become aligned with the lower smooth section of the coping member such that there is no longer a threaded relationship between the bolt member and the coping member because their respective threaded portions are disengaged.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 2 is a cross-sectional view of the coping member of the present invention two-piece interlockable impression coping taken along line 2—2 of FIG. 1.

FIG. 5 is a perspective view of the bolt member of the present invention two-piece interlockable impression coping.

FIG. 9 is a cross-sectional view showing that the present invention two-piece impression coping fully fastened to the dental implant fixture.

DESCRIPTION OF THE PREFERRED EMBODIMENT

Figure 1:
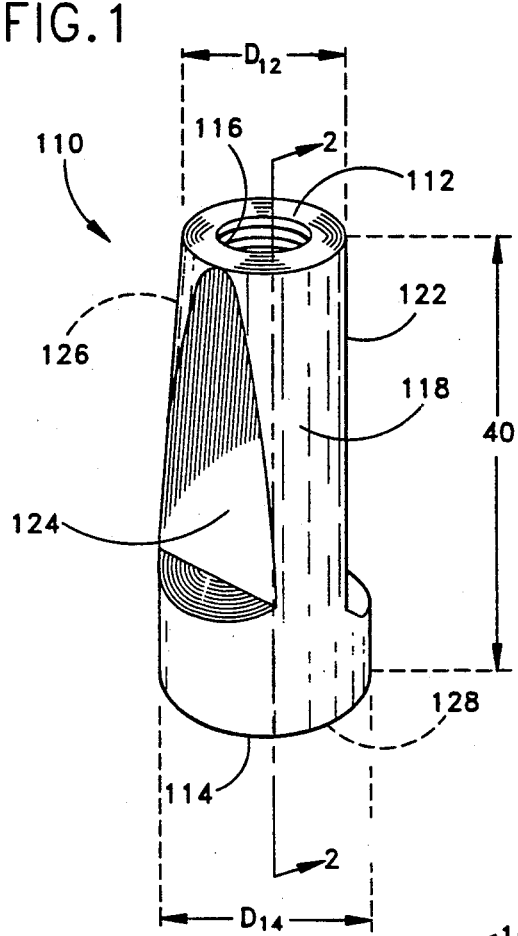
FIG. 1 is a perspective view of the coping member of the present invention two-piece interlockable impression coping.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Referring to FIGS. 1 through 4, there is shown at 110 the coping member of the present invention two-piece interlockable impression coping. The coping member 110 has a generally frusto-conical or cylindrical shaped configuration. It has a small distal end 112 and a large proximal end 114. It also has an interior bore 116 and an exterior sidewall 118. The exterior sidewall 118 has three flattened surfaces 122, 124 and 126. Flat surfaces 124 and 126 are adjacent to one another and symmetrically disposed to form a triangle. Flat surface 122 is remote from flat surfaces 124 and 126, and is perpendicular to the surface which equally divides the triangle. The flattened surfaces on the exterior sidewall 118 of the coping member 110 are provided as means for preventing an impression from rotating about the coping member 110 and for the proper realignment between the impression and the coping member 110. It will be appreciated that the number, dimensions, locations and orientations of the flattened surfaces may vary.

The proximal end 114 of the coping member has a female hexagonal interface 128. The function of the female hexagonal interface 128 will be described later in detail.

The novelty of the present invention includes the unique structure of the interior bore 116 of the coping member 110. The uniqueness of the interior bore 116 of the coping member 110 is that it is a stepped bore having two sections: a distal section 132 and a proximal section 134. The two sections of the interior bore 116 of the coping member 110 are completely different and complement each other: the distal section 132 is short, the proximal section 134 is long; the distal section 132 is narrow, the proximal section 134 is wide; and finally, the distal section 132 has inner screw threads 136, and the proximal section 134 has a smooth interior sidewall 138. This design and construction of interior bore 116 of the coping member 110 serves the special objects of the present invention, which will be described in detail later.

The following dimensions and their relationships of one preferred embodiment of the present invention coping member 110 are illustrated in FIGS. 1 through 4. The diameter of the small distal end 112 of the coping member 110 is D12, and the diameter of the large proximal end 114 of the coping member 110 is D14. D14 is larger than D12, $$D14 > D12.$$

The diameter of the threaded distal section 132 of the interior bore 116 of the coping member 110 is D16, and the diameter of the smooth proximal section of the interior bore 116 of the coping member 110 is D18. D18 is larger than D16, $$D18 > D16.$$

Moreover, the diameter D12 of the small distal end 112 of the coping member 110 is larger than the diameter D18 of the smooth proximal section of the interior bore 116 of the coping member 110, $$D12 > D18.$$

Therefore, the relationship between the four diameters is:

$$D14 > D12 > D18 > D16.$$

In addition, the total length of the coping member 110 is L10, the length of the threaded distal section 132 of the interior bore 116 of the coping member 110 is L12, and the length of the smooth proximal section of the interior bore 116 of the coping member 110 is L14. Of course the total length L10 is larger than the sum of the two lengths L12 and L14, $$L10 > L12 + L14.$$

The bolt member of the present invention two-piece impression coping is shown in FIG. 5 at 140. The bolt member 140 has a head part 142 and an elongated shaft part 144. The shaft part 144 again has two sections: a distal section 146 which is smooth, and a proximal section 148 which has screw threads compatible with the inner screw threads 136 of the distal section 132 of the interior bore 116 of the coping member 110. A notch 150 is provided at the head part 142 for accommodating a driving tool such as a screwdriver. The total length of the shaft part 144 of the bolt member 140 is L20, the length of the smooth distal section 146 of the shaft part 144 of the bolt member 140 is L22, and the length of the threaded proximal section 148 of the shaft part 144 of the bolt member 140 is L24. Of course, $$L20 = L22 + L24.$$

The diameter D24 of the threaded section 148 of the shaft part 144 of the bolt member 140 is in conformity with the diameter D16 of the distal section 132 of the interior bore 116 of the coping member 110 to ensure the compatibility, i.e., D24 is approximately equal to D16, $$D24 = D16.$$

Figure 6:
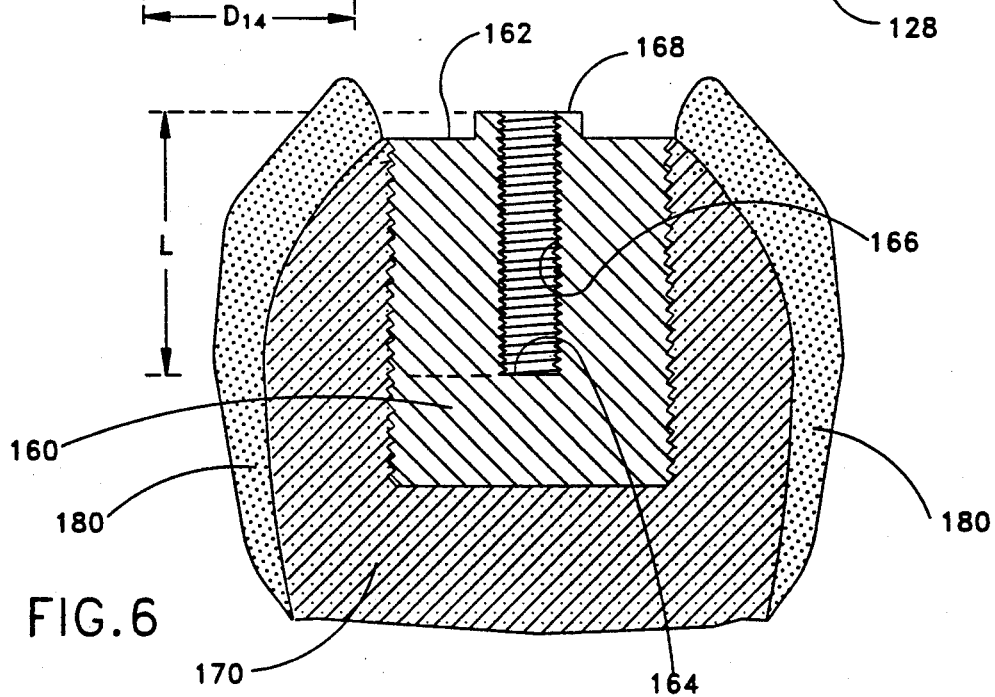
FIG. 6 is a cross-sectional view showing a typical dental implant fixture.
Figures 3, 4:
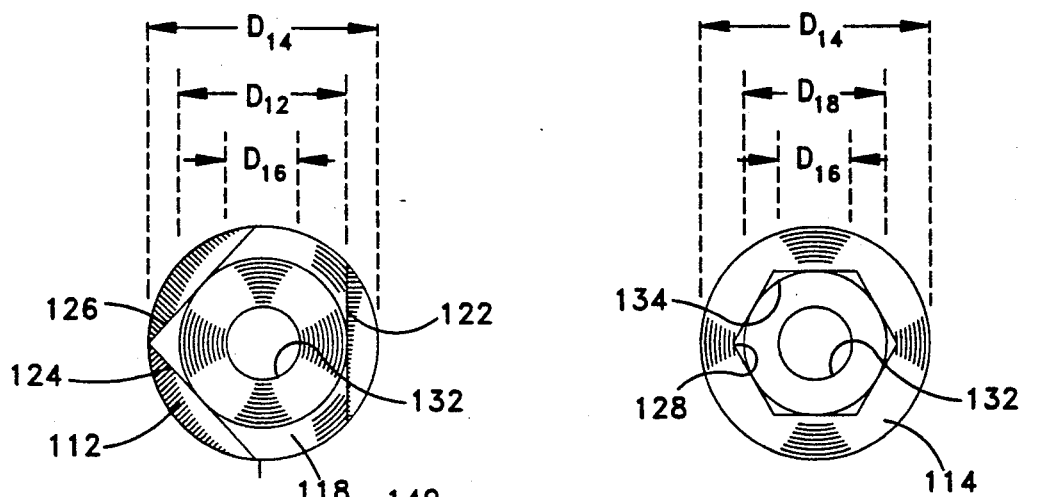
FIG. 3 is a top view of the coping member of the present invention two-piece interlockable impression coping.
FIG. 4 is a bottom view of the coping member of the present invention two-piece interlockable impression coping.

The present invention impression coping is used for making a dental impression of dental implant fixture or other components such as an abutment. A typical dental implant fixture 160 is shown in FIG. 6. The dental fixture 160 is implanted in a patient's jawbone 170, which is surrounded by gingiva 180. The implant fixture has an exposed end 162, and a hollow portion 164 opened from the exposed end 162 and extending into the implant fixture 160. The hollow portion 164 has inner screw threads 166. The implant fixture further has a male hexagonal interface 168 at its exposed end 162. The hollow portion 164 of the implant fixture 160 is provided for accommodating the bolt member 140. Therefore, the threaded proximal section 148 of the shaft part 144 of the bolt member 140 is compatible with the inner screw threads 166 of the hollow portion 164 of the implant fixture 160. It is also important that the depth L of the hollow portion 164 of the implant fixture 160 is large enough to accommodate the threaded proximal section 148 of the shaft part 144 of the bolt member 140.

Figure 7:
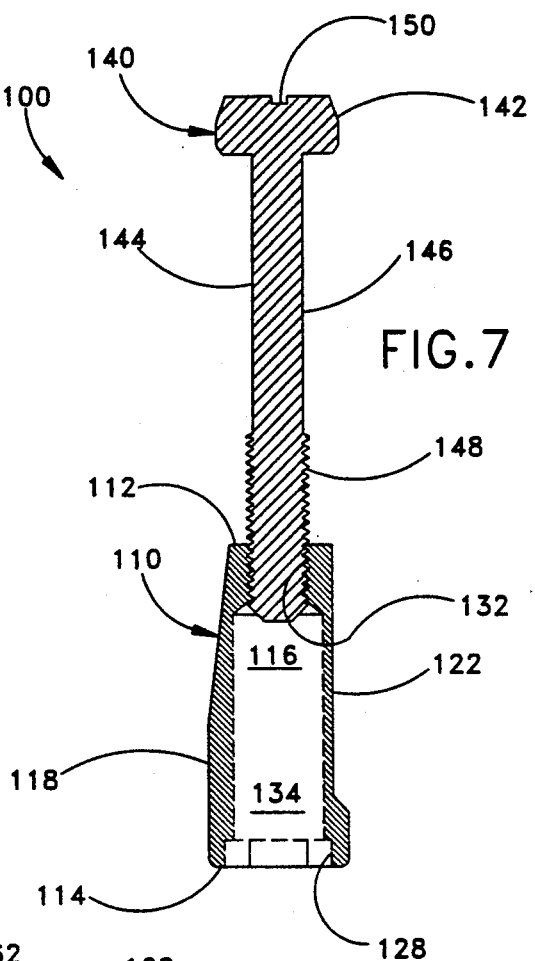
FIG. 7 is a cross-sectional view showing that the coping member and the bolt member are interlocked with each other.

Another novel feature of the present invention is that the coping member 110 and the bolt member 140 are interlockable, i.e. they can be coupled together before they are placed onto the implant fixture 160 inside a patient's oral cavity. This is a critical advantage of the present invention impression coping over prior art impression copings. Referring to FIG. 7, there is shown at 100 the present invention two-piece impression coping as a unitary assembly. The coping member 110 and the bolt member 140 can be interlocked together by threading the threaded section 148 of the shaft part 144 of the bolt member 140 into the distal section 132 of the interior bore 116 of the coping member 110, from the distal end 112 of the coping member 110. By having the coping member 110 and the bolt member 140 interlocked, the present invention two-piece impression coping 100 can be handled together as a larger unit, which reduces the possibility of either dropping or losing the coping member 110 or the bolt member 140 in the patient's oral cavity. It also reduces the possibility of mismatching pairs of different configurations or dimensions.

Figure 8:
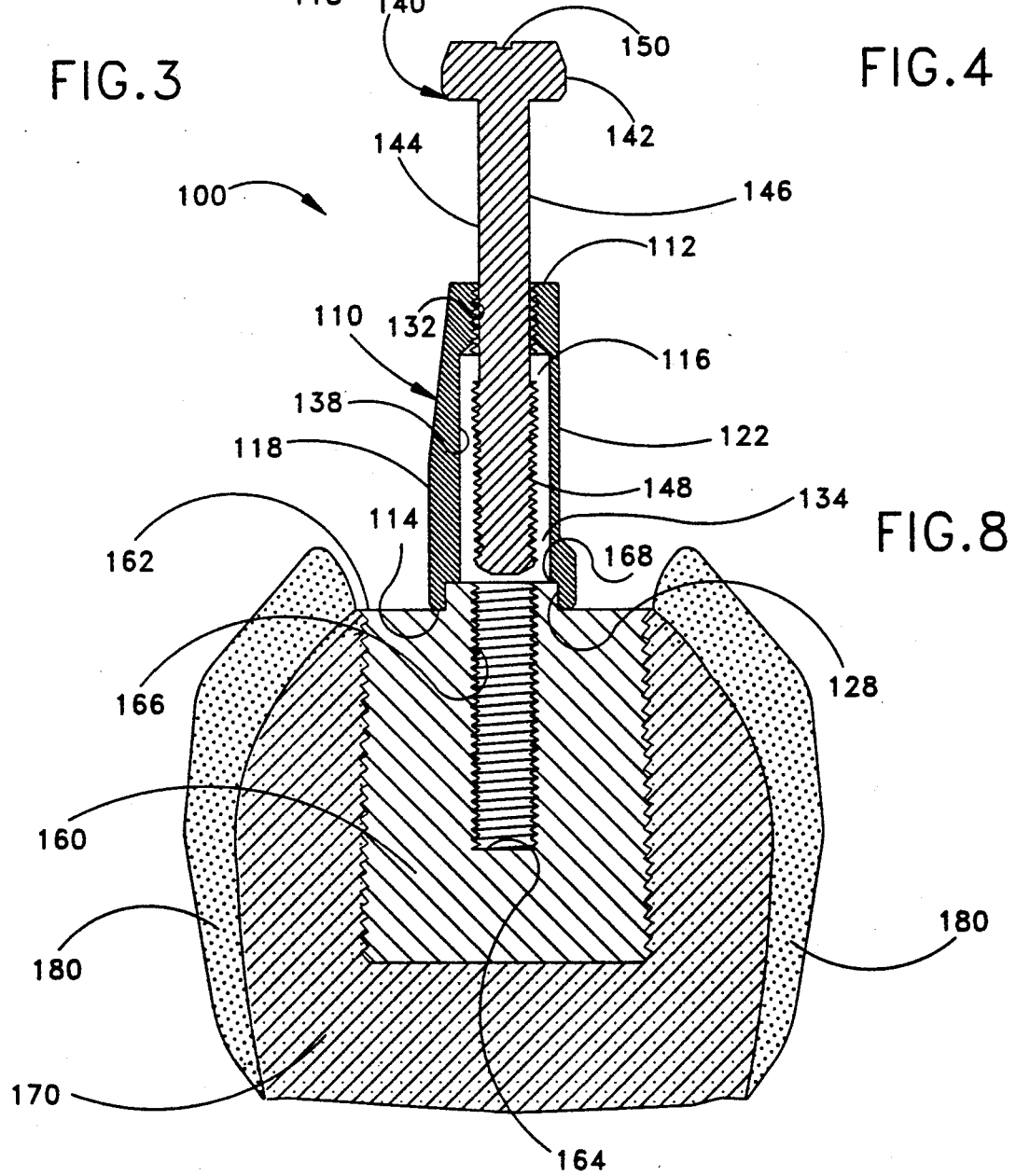
FIG. 8 is a cross-sectional view showing that the present invention two-piece impression coping is placed on the dental implant fixture before they are fastened.

Referring to FIGS. 8 and 9, there is shown the following steps of fastening the coping member 110 with the bolt member 140. Shown in FIG. 8, the coping member 110 is placed onto the exposed end 162 of the implant fixture 160 with the bolt member 140 attached. The female hexagonal interface 128 at the proximal end 114 of the coping member 110 is fully engaged with the male hexagonal interface 168 at the exposed end 162 of the implant fixture 160. This hexagonal connection prevents the coping member 110 from rotating about the implant fixture 160, which is critical for making an accurate dental impression for transferring the exact position and orientation of the implant fixture 160. It is appreciated that other polygonal interfaces, or other means for preventing the rotation between the coping member 110 and the implant fixture 160, may be utilized.

Once the coping member 110 is firmly seated on the exposed end 162 of the implant fixture 160 and the male hexagonal interface 168 at the exposed end 162 of the implant fixture 160 is fully engaged with the female hexagonal interface 128 at the proximal end 114 of the coping member 110, the shaft part 144 of the bolt member 140 can be further threaded into interior bore 116 of the coping member 110.

It is important that the length $L_{22}$ of the smooth distal section 146 of the shaft part 144 of the bolt member 140 is larger than the length $L_{12}$ of the threaded distal section 132 of the interior bore 116 of the coping member 110, $$L_{22} > L_{12}$$

so that the threaded proximal section 148 of the shaft part 144 of the bolt member 140 can be completely threaded through, and finally disengaged from, the threaded distal section 132 of the interior bore 116 of the coping member 110. At this point the threaded proximal section 148 of the shaft part 144 of the bolt member 140 is located within the smooth proximal section 134 of the interior bore 116 of the coping member 110.

It is important that the length $L_{24}$ of the threaded proximal section 148 of the shaft part 144 of the bolt member 140 is smaller than the length $L_{14}$ of the smooth proximal section 134 of the interior bore 116 of the coping member 110, $$L_{14} > L_{14}$$

so that there will be no possibility of the threaded proximal section 148 of the shaft part 144 of the bolt member 140 becoming engaged threadedly with both the threaded distal section 132 of the interior bore 116 of the coping member 110 and the threaded hollow portion 164 of the implant fixture 160. This is critical because if the bolt member 140 is threadedly engaged with both the coping member 110 and the implant fixture 160, then on the one hand, when the bolt member 140 has a threaded relationship with the coping member 110, it applies not only a downward translational force but also a torque to the coping member 110. The translational force will act to fasten the coping member 110 to the implant fixture 160, but the torque will act to rotate the coping member 110 about the implant fixture 160. This will defeat the purpose of having the hexagonal connection between the coping member 110 and the implant fixture 160 which is to prevent the coping member from rotating about the implant fixture 160.

Therefore, the novelty of the present invention further includes that the threaded distal section 132 of the interior bore 116 of the coping member 110 is purposely designed and constructed to be offset from the threaded proximal section 148 of the shaft part 144 of the bolt member 140, when the coping member 110 is fastened to the implant fixture 160 by the bolt member 140. This will ensure that when the bolt member 140 is threadedly engaged with the implant fixture 160, the coping member 110 is no longer threadedly engaged with the bolt member 140 to avoid any incompatibility with the hexagonal connection between the coping member 110 and the implant fixture 160.

Shown in FIG. 9, the present invention two-piece impression coping 100 is fully fastened to the dental implant fixture 160. The head part 142 of the bolt member 140 is contacting the distal end 112 of the coping member 110, and the threaded proximal section 148 of the shaft part 144 of the bolt member 140 is threaded into the threaded hollow portion 164 of the implant fixture. It is important that the total length $L_{20}$ of the shaft part 144 of the bolt member 140 is larger than the total length $L_{10}$ of the coping member 110, $$L_{20} > L_{10}$$

so that a substantial portion of the threaded proximal section 148 of the shaft part 144 of the bolt member 140 is threadedly engaged with the inner screw threads 166 of the hollow portion 164 of the implant fixture 160.

The present invention two-piece interlockable impression coping 100 can be used with not only dental implant fixtures, but other dental components such as dental abutments as well. When used with a dental abutment, the present invention two-piece interlockable impression coping 100 will ensure that an impression will be made which transfers accurate position and orientation of the abutment.

The present invention is not only an apparatus, but also a novel method of attaching the impression coping to the implant fixture. The essential uniqueness of the present invention method is to interlock the coping piece and the bolt piece so they can be handled together which greatly reduces the risk of having one of the pieces dropped or lost in the patient's oral cavity. It also reduces the risk of having different shaped and sized coping members and bolt members mismatched.

Defined in detail, the present invention is an impression coping attachable to a dental fixture for making an impression, which fixture is implanted into a patient's jawbone and has an exposed end with a hexagonal interface and a hollow portion with inner screw threads, the impression coping comprising: (a) a bolt member having a head part and an elongated shaft part, the shaft part having a proximal end and a distal end, and the head part integrally connected to the distal end of the shaft part; (b) said shaft part of said bolt member having a proximal section and a distal section, the proximal section having outer screw threads compatible with said inner screw threads of said hollow portion of said implant fixture; (c) a generally frusto-conical shaped coping member having a large proximal end, a small distal end, a stepped interior bore extending from the distal end to the proximal end, and an exterior sidewall; (d) said proximal end of said coping member having a complementary hexagonal interface engagable with said hexagonal interface at said exposed end of said implant fixture for preventing said coping member from rotating about said implant fixture; (e) said exterior sidewall of said coping member having a multiplicity of flattened inclined surfaces for preventing said impression from rotating about said coping member; (f) said interior bore of said coping member having a wide proximal section and a narrow distal section, the proximal section being smooth, and the distal section having inner screw threads compatible with said outer screw threads of said proximal section of said shaft part of said bolt member; (g) said coping member and said bolt member being interlockable by threading said proximal section of said shaft part of said bolt member into said distal section of said interior bore of said coping member; (h) said distal section of said shaft part of said bolt member being longer than said distal section of said interior bore of said coping member, such that after said proximal section of said shaft part of said bolt member is completely threaded through said distal section of said interior bore of said coping member from said distal end of said coping member, said coping member and said bolt member are not threadably engaged; (i) said proximal section of said interior bore of said coping member being wider than said proximal section of said shaft part of said bolt member such that when said proximal section of said shaft part of said bolt member is located within said proximal section of said interior bore of said coping member, said proximal section of said interior bore of said coping member is completely disengaged from said proximal section of said shaft part of said bolt member; (j) said proximal section of said interior bore of said coping member being longer than said proximal section of said shaft part of said bolt member, such that when said complementary hexagonal interface at said proximal end of said coping member is fully engaged with said hexagonal interface at said exposed end of said implant fixture, said proximal section of said shaft part of said bolt member cannot be threadably engaged with said proximal section of said interior bore of said coping member and said hollow portion of said implant fixture simultaneously; and (k) said shaft part of said bolt member being longer than said coping member, such that after said shaft part of said bolt member extends through said interior bore of said coping member from said distal end of said coping member, there is still a substantial portion of said proximal section of said shaft part of said bolt member which can be threadably engaged with said hollow portion of said implant fixture for fastening said coping member to said exposed end of said implant fixture; (l) whereby said coping member and said bolt member is threadably interlocked before said bolt member is threadably engaged with said implant fixture, but are not threadably engaged when said bolt member are threadably engaged with said implant fixture, such that the hexagonal connection between said coping member and said implant fixture is not jeopardized.

Defined broadly, the present invention is an impression coping attachable to a dental component of an anatomical dental abutment restorative system for making an impression, which dental component has a distal end with a polygonal interface and a threaded hollow, the impression coping comprising: (a) an elongated bolt member having a proximal end, a widened distal end and a threaded section adjacent to the proximal end engagable with said threaded hollow at said distal end of said dental component; (b) a generally cylindrical shaped coping member having a proximal end, a distal end, an interior bore extending from the distal end to the proximal end, and an exterior sidewall; (c) said proximal end of said coping member having a complementary polygonal interface engagable with said polygonal interface at said distal end of said dental component for preventing said coping member from rotating about said dental component; (d) said exterior sidewall of said coping member having at least one flattened surface for preventing said impression from rotating about said coping member; (e) most of said interior bore of said coping member being smooth but having a threaded section engagable with said threaded section of said bolt member; and (f) said threaded section of said coping member and said threaded section of said bolt member being offset, such that when said complementary polygonal interface at said proximal end of said coping member is fully engaged with said polygonal interface at said distal end of said dental component, said threaded section of said bolt member will not be threadably engaged with said threaded section of said interior bore of said coping member and said threaded hollow of said dental component simultaneously; (g) whereby said coping member and said bolt member are threadably interlocked before said bolt member is threadably engaged with said dental component, but are not threadably engaged when said bolt member is threadably engaged with said dental component, such that the polygonal connection between said coping member and said dental component is not jeopardized.

Defined more broadly, the present invention is an impression coping attachable to a dental component of an anatomical dental abutment restorative system for making an impression, which dental component has a threaded hollow and means for preventing relative rotation between the coping and the dental component, the impression coping comprising: (a) a bolt member having a threaded section engagable with said threaded hollow of said dental component; (b) a coping member having an interior bore for allowing said bolt member to extend through the coping member; (c) said coping member having means for engagement with said rotation preventing means of said dental component to prevent said coping member from rotating about said dental component; (d) said coping member further having means for preventing said impression from rotating about said coping member; (e) most of said interior bore of said coping member being otherwise smooth but having a threaded section engagable with said threaded section of said bolt member; and (f) said threaded section of said coping member and said threaded section of said bolt member being offset, such that when said complementary anti-rotation means of said coping member is fully engaged with said anti-rotation means of said dental component, said threaded section of said bolt member will not be threadably engaged with said threaded section of said interior bore of said coping member and said threaded hollow of said dental component simultaneously; (g) whereby said coping member and said bolt member are threadably interlocked before said bolt member are threadably engaged with said dental component, but are not threadably engaged when said bolt member is threadably engaged with said dental component, such that the anti-rotation connection between said coping member and said dental component is not jeopardized.

Defined even more broadly, the present invention is an impression coping attachable to a dental component of an anatomical dental abutment restorative system for making an impression, the impression coping comprising a bolt member and a coping member having complementary intercoupling means respectively, which intercoupling means are disengaged when said coping member is fully fastened to said dental component by said bolt member.

Alternatively defined in detail, the present invention is a method of attaching an impression coping to a dental fixture implanted in a patient's jawbone for making an impression, which fixture has a hexagonal interface and a threaded hollow, the method comprising the steps of: (a) utilizing an elongated bolt member which has a threaded proximal section engagable with said threaded hollow of said implant fixture and a smooth distal section; (b) utilizing a generally frusto-conical shaped coping member which has a stepped interior bore including a smooth and widened proximal section and a threaded distal section, a complementary hexagonal interface engagable with said hexagonal interface of said dental component for preventing the coping member from rotating about said dental component, and at least one flattened exterior surface for preventing said impression from rotating about the coping member; (c) interlocking said coping member and said bolt member by threading said proximal section of said bolt member into said distal section of said interior bore of said coping member; (d) attaching said coping member with said interlocked bolt member onto said implant fixture by fully engaging said complementary hexagonal interface of said coping member with said hexagonal interface of said implant fixture; and (e) fastening said coping member to said implant fixture by threading said bolt member until its threaded proximal section is completely disengaged with said threaded distal section of said coping member, and instead engaged with said threaded hollow of said implant fixture; (f) whereby said coping member and said bolt member are threadably interlocked before said bolt member is threadably engaged with said implant fixture, but are not threadably engaged when said bolt member is threadably engaged with said implant fixture, such that the hexagonal interface between said coping member and said implant fixture is not jeopardized.

Alternatively defined broadly, the present invention is a method of attaching an impression coping to a dental component of an anatomical dental abutment restorative system for making an impression, which dental component has a threaded hollow and means for preventing the relative rotation between the coping and the dental component, the method comprising the steps of: (a) utilizing a bolt member which has a threaded section engagable with said threaded hollow of said dental component; (b) utilizing a coping member which has an interior bore including a threaded section offset from said threaded section of said bolt member, means engagable with said rotation preventing means of said dental component for preventing said coping member from rotating about said dental component, and means for preventing said impression from rotating about said coping member; (c) interlocking said coping member and said bolt member by threading said threaded section of said bolt member into said threaded section of said interior bore of said coping member; (d) attaching said coping member with said interlocked bolt member onto said dental component by fully engaging said respective rotation preventing means; and (e) fastening said coping member to said dental component by threading said bolt member until its threaded section is completely disengaged with said threaded section of said coping member, and instead engaged with said threaded hollow of said dental component; (f) whereby said coping member and said bolt member are threadably interlocked before said bolt member is threadably engaged with said dental component, but are not threadably engaged when said bolt member is threadably engaged with said dental component, such that the rotation preventing connection between said coping member and said implant fixture is not jeopardized.

Alternatively defined more broadly, the present invention is a method for attaching an impression coping to a dental component of an anatomical dental abutment restorative system for making an impression, including the steps of utilizing a bolt member and a coping member which have complementary intercoupling means respectively, intercoupling the bolt member and the coping member, attaching the coping member to the dental component and fastening the coping member to the dental component by the bolt member while having the complementary intercoupling means disengaged.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modification in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. An impression coping attachable to a dental component of an anatomical dental abutment restorative system for making an impression, which dental component has a threaded hollow and means for preventing relative rotation between the coping and the dental component, the impression coping comprising:

a. a bolt member having a threaded section engagable with said threaded hollow of said dental component;

b. a coping member having an interior bore for allowing said bolt member to extend through the coping member;

c. said coping member having means for engagement with said rotation preventing means of said dental component to prevent said coping member from rotating about said dental component;

d. said coping member further having means for preventing said impression from rotating about said coping member;

e. most of said interior bore of said coping member being smooth but having a threaded section engagable with said threaded section of said bolt member; and f. said threaded section of said coping member and said threaded section of said bolt member being offset, such that when said complementary anti-rotation means of said coping member is fully engaged with said anti-rotation means of said dental component, said threaded section of said bolt member will not be threadably engaged with said threaded section of said interior bore of said coping member and said threaded hollow of said dental component simultaneously;

g. whereby said coping member and said bolt member are threadably interlocked before said bolt member is threadably engaged with said dental component, but are not threadably engaged when said bolt member is threadably engaged with said dental component, such that the anti-rotation connection between said coping member and said dental component is not jeopardized.

2. The invention as defined in claim 1 wherein said bolt member has means cooperable with a driving tool.

3. The invention as defined in claim 1 wherein said means of said dental component for preventing relative rotation is a male hexagonal interface.

4. The invention as defined in claim 3 wherein said means of said coping member for preventing said coping member from rotating about said dental component is a female hexagonal interface.

5. The invention as defined in claim 1 wherein said means of said coping member for preventing said impression from rotating about said coping member includes at least one flattened surface.

6. The invention as defined in claim 1 wherein said bolt member is longer than said coping member, such that after said bolt member extends through said interior bore of said coping member, there is still a substantial portion of said threaded section of said bolt member for threaded engagement with said threaded hollow of said dental component for fastening said coping member to said dental component.

7. An impression coping attachable to a dental component of an anatomical dental abutment restorative system for making an impression, which dental component has a distal end with a polygonal interface and a threaded hollow, the impression coping comprising:

a. an elongated bolt member having a proximal end, a widened distal end and a threaded section adjacent to the proximal end engagable with said threaded hollow at said distal end of said dental component;

b. a generally cylindrical shaped coping member having a proximal end, a distal end, an interior bore extending from the distal end to the proximal end, and an exterior sidewall;

c. said proximal end of said coping member having a complementary polygonal interface engagable with said polygonal interface at said distal end of said dental component for preventing said coping member from rotating about said dental component;

d. said exterior sidewall of said coping member having at least one flattened surface for preventing said impression from rotating about said coping member;

e. most of said interior bore of said coping member being smooth but having a threaded section engagable with said threaded section of said bolt member; and f. said threaded section of said coping member and said threaded section of said bolt member being offset, such that when said complementary polygonal interface at said proximal end of said coping member is fully engaged with said polygonal interface at said distal end of said dental component, said threaded section of said bolt member will not be threadably engaged with said threaded section of said interior bore of said coping member and said threaded hollow of said dental component simultaneously;

g. whereby said coping member and said bolt member are threadably interlocked before said bolt member is threadably engaged with said dental component, but are not threadably engaged when said bolt member is threadably engaged with said dental component, such that the polygonal connection between said coping member and said dental component is not jeopardized.

8. The invention as defined in claim 7 wherein said widened distal end of said bolt member has means cooperable with a driving tool.

9. The invention as defined in claim 7 wherein said polygonal interface at said distal end of said dental component is a male hexagonal interface.

10. The invention as defined in claim 9 wherein said complementary polygonal interface at said proximal end of said coping member is a female hexagonal interface.

11. The invention as defined in claim 7 wherein the length of said threaded section of said bolt member is less than half of the total length of said bolt member.

12. The invention as defined in claim 7 wherein said threaded section of said coping member is less than half of the total length of said coping member.

13. The invention as defined in claim 7 wherein said bolt member is longer than said coping member, such that after said bolt member extends through said interior bore of said coping member from said distal end of said coping member, there is still a substantial portion of said threaded section of said bolt member for threaded engagement with said threaded hollow of said dental component for fastening said coping member to said distal end of said dental component.

14. An impression coping attachable to a dental fixture for making an impression, which fixture is implanted into a patient's jawbone and has an exposed end with a hexagonal interface and a hollow portion with inner screw threads, the impression coping comprising:

a. a bolt member having a head part and an elongated shaft part, the shaft part having a proximal end and a distal end, and the head part integrally connected to the distal end of the shaft part;

b. said shaft part of said bolt member having a proximal section and a distal section, the proximal section having outer screw threads compatible with said inner screw threads of said hollow portion of said implant fixture;

c. a generally frusto-conical shaped coping member having a large proximal end, a small distal end, a stepped interior bore extending from the distal end of the coping member to the proximal end of the coping member and an exterior sidewall;

d. said proximal end of said coping member having a complementary hexagonal interface engagable with said hexagonal interface at said exposed end of said implant fixture for preventing said coping member from rotating about said implant fixture;

e. said exterior sidewall of said coping member having a multiplicity of flattened inclined surfaces for preventing said impression from rotating about said coping member;

f. said interior bore of said coping member having a wide proximal section and a narrow distal section, the proximal section of the bore being smooth, and the distal section of the bore having inner screw threads compatible with said outer screw threads of said proximal section of said shaft part of said bolt member;

g. said coping member and said bolt member being interlockable by threading said proximal section of said shaft part of said bolt member into said distal section of said interior bore of said coping member;

h. said distal section of said shaft part of said bolt member being longer than said distal section of said interior bore of said coping member, such that after said proximal section of said shaft part of said bolt member is completely threaded through said distal section of said interior bore of said coping member from said distal end of said coping member, said coping member and said bolt member are not threadably engaged;

i. said proximal section of said interior bore of said coping member being wider than said proximal section of said shaft part of said bolt member, such that when said proximal section of said shaft part of said bolt member is located within said proximal section of said interior bore of said coping member, said proximal section of said interior bore of said coping member is completely disengaged from said proximal section of said shaft part of said bolt member;

j. said proximal section of said interior bore of said coping member being longer than said proximal section of said shaft part of said bolt member, such that when said complementary hexagonal interface at said proximal end of said coping member is fully engaged with said hexagonal interface at said exposed end of said implant fixture, said proximal section of said shaft part of said bolt member cannot be threadably engaged with said proximal section of said interior bore of said coping member and said hollow portion of said implant fixture simultaneously; and k. said shaft part of said bolt member being longer than said coping member, such that after said shaft part of said bolt member extends through said interior bore of said coping member from said distal end of said coping member, there is still a substantial portion of said proximal section of said shaft part of said bolt member which can be threadably engaged with said hollow portion of said implant fixture for fastening said coping member to said exposed end of said implant fixture;

l. whereby said coping member and said bolt member are threadably interlocked before said bolt member is threadably engaged with said implant fixture, but are not threadably engaged when said bolt member is threadably engaged with said implant fixture, such that the hexagonal connection between said coping member and said implant fixture is not jeopardized.

15. The invention as defined in claim 14 wherein said head part of said bolt member has means cooperable with a driving tool.

16. The invention as defined in claim 14 wherein said hexagonal interface at said exposed end of said implant fixture is a male hexagonal interface.

17. The invention as defined in claim 16 wherein said complementary hexagonal interface at said proximal end of said coping member is a female hexagonal interface.

18. The invention as defined in claim 14 wherein said multiplicity of flattened surfaces including three flat surfaces, wherein one flat surface is remote from the other two flat surfaces which are adjacent and symmetrically disposed.

19. A method of attaching an impression coping to a dental fixture implanted in a patient's jawbone for making an impression, which fixture has a hexagonal interface and a threaded hollow, the method comprising the steps of:

a. utilizing an elongated bolt member which has a threaded proximal section engagable with said threaded hollow of said implant fixture and a smooth distal section;

b. utilizing a generally frusto-conical shaped coping member which has a stepped interior bore including a smooth and widened proximal section and a threaded distal section, a complementary hexagonal interface engagable with said hexagonal interface of said dental component for preventing the coping member from rotating about said dental component, and at least one flattened exterior surface for preventing said impression from rotating about the coping member;

c. interlocking said coping member and said bolt member by threading said proximal section of said bolt member into said distal section of said interior bore of said coping member;

d. attaching said coping member with said interlocked bolt member onto said implant fixture by fully engaging said complementary hexagonal interface of said coping member with said hexagonal interface of said implant fixture; and e. fastening said coping member to said implant fixture by threading said bolt member until its threaded proximal section is completely disengaged with said threaded distal section of said coping member, and instead engaged with said threaded hollow of said implant fixture;

f. whereby said coping member and said bolt member are threadably interlocked before said bolt member is threadably engaged with said implant fixture, but are not threadably engaged when said bolt member is threadably engaged with said implant fixture, such that the hexagonal interface between said coping member and said implant fixture is not jeopardized.

20. The invention as defined in claim 19 further comprising the step of packaging, transporting and storing said coping member and said bolt member as they are interlocked.

21. A method of attaching an impression coping to a dental component of an anatomical dental abutment restorative system for making an impression, which dental component has a threaded hollow and means for preventing the relative rotation between the coping and the dental component, the method comprising the steps of:
 a. utilizing a bolt member which has a threaded section engagable with said threaded hollow of said dental component;
 b. utilizing a coping member which has an interior bore including a threaded section offset from said threaded section of said bolt member, means engagable with said rotation preventing means of said dental component for preventing said coping member from rotating about said dental component, and means for preventing said impression from turning about said coping member;
 c. interlocking said coping member and said bolt member by threading said threaded section of said bolt member into said threaded section of said interior bore of said coping member;
 d. attaching said coping member with said interlocked bolt member onto said dental component by fully engaging said respective rotation preventing means; and
 e. fastening said coping member to said dental component by threading said bolt member until its threaded section is completely disengaged with said threaded section of said coping member, and instead engaged with said threaded hollow of said dental component;
 f. whereby said coping member and said bolt member are threadably interlocked before said bolt member is threadably engaged with said dental component, but are not threadably engaged when said bolt member is threadably engaged with said dental component, such that the rotation preventing connection between said coping member and said implant fixture is not jeopardized.

22. The invention as defined in claim 21 further comprising the step of packaging, transporting and storing said coping member and said bolt member as they are interlocked.

* * * * *